United States Patent [19]

Baylis

[11] Patent Number: 5,532,205
[45] Date of Patent: Jul. 2, 1996

[54] HERBICIDAL COMPOSITION CONTAINING GLYPHOSATE OR A SALT THEREOF

[75] Inventor: Alan D. Baylis, Binfield, United Kingdom

[73] Assignee: Zeneca Limited, London, England

[21] Appl. No.: 201,830

[22] Filed: Feb. 25, 1994

[30] Foreign Application Priority Data

Mar. 3, 1993 [GB] United Kingdom ............. 9304294

[51] Int. Cl.$^6$ .................... A01N 57/12; A01N 57/20
[52] U.S. Cl. .................. 504/128; 504/130; 504/136
[58] Field of Search ................... 504/127, 128, 504/206

[56] References Cited

U.S. PATENT DOCUMENTS

| | | | |
|---|---|---|---|
| 3,799,758 | 3/1974 | Franz | 504/206 |
| 4,075,002 | 2/1978 | Drewe et al. | 504/245 |
| 5,078,781 | 1/1992 | Finch, Jr. | 504/130 |

FOREIGN PATENT DOCUMENTS

| | | |
|---|---|---|
| 192583 | 8/1986 | European Pat. Off. . |
| 297305 | 1/1989 | European Pat. Off. . |
| 475392 | 3/1992 | European Pat. Off. . |
| 9104367 | 3/1992 | South Africa . |
| 2169806 | 1/1985 | United Kingdom . |
| 2100603 | 1/1993 | United Kingdom . |

OTHER PUBLICATIONS

Research Disclosure, Jun. 1973, pp. 62–65.
Chem. Abstr. 114, 116817y (1991).
Chem. Abstr. 97, 201320h (1982).
Faiz et al., Proc. Int. Conf. Plant Prot. in Tropics. pp. 531–541 (1982).
Maldonado, Rumipamba, pp. 55–70 (1986); Weed Abstracts, vol. 36, No. 2118 (1987).
Gomes, Weed Abstracts, vol. 35, No. 2813 (1984).
Fadayomi et al., Biological Abstracts No. 79046006 (1984).
Imperial Chemical Industries PLC Brochure–"Gramocil" Information Bulletin (1984).

*Primary Examiner*—Gary E. Hollinden
*Assistant Examiner*—B. Bembenick
*Attorney, Agent, or Firm*—Joel G. Ackerman

[57] ABSTRACT

A herbicidal composition comprising (i) N-phosphonomethylglycine or an agriculturally acceptable salt thereof in combination with (ii) paraquat or diquat or a mixture thereof and (iii) a herbicide which functions as a photosystem II inhibitor, for example diuron, chlortoluron, isoproturon, linuron, tebuthiuron, bentazone, oxadiazon, bromacil, ametryne, atrazine, cyanazine, hexazinone, metribuzin, simazine or terbuthylazine.

11 Claims, No Drawings

HERBICIDAL COMPOSITION CONTAINING GLYPHOSATE OR A SALT THEREOF

This invention relates to a herbicidal composition and in particular to a herbicidal composition containing N-phosphonomethylglycine (glyphosate) or a salt thereof.

N-phosphonomethylglycine and its salts such as the trimethylsulphonium or isopropylamine salts are well known as highly active herbicides which achieve excellent control of weed species together with an effective reduction in regrowth. Such herbicides tend however to be relatively slow acting and no visible evidence of adverse symptoms is generally apparent during the first few days after application. For a number of commercial applications it is desirable for evidence of plant damage to be readily apparent to the eye within a few days following application of the herbicide; i.e. that the herbicide should exhibit early burndown symptoms.

It is known to combine glyphosate herbicides with certain contact herbicides exhibiting early burndown symptoms. International Publication WO 92/11764 for example describes a herbicidal formulation comprising an agriculturally acceptable salt of N-phosphonomethylglycine and an effective amount of at least one $C_5$ to $C_{16}$ agriculturally acceptable fatty acid or salt thereof. It is often the case however that visible early burndown symptoms such as desiccation, leaf-burn, necrosis and wilting may only be achieved at the expense of a reduction in long term control and inhibition of re-growth.

The bipyridyl herbicides paraquat and diquat are well known contact herbicides which cause severe damage to plant tissue and as a consequence show early burndown symptoms.

A relatively effective herbicidal composition may be achieved by combining N-phosphonomethylglycine or an agriculturally acceptable salt thereof with the herbicide diquat or the herbicide paraquat. At a ratio of about 5 parts by weight of diquat or paraquat to 100 parts by weight of the agriculturally acceptable salt of N-phosphonomethylglycine a composition is obtained which produces some visible evidence of early burndown symptoms but at the cost of some reduction in long term and re-growth control. Compositions containing a significantly higher proportion of diquat or paraquat produce more effective early burndown symptoms but only in combination with markedly reduced long term and re-growth control. Conversely, compositions containing a significantly lower proportion of diquat or paraquat provide little by way of visible early burndown symptoms.

We have now found that a highly effective herbicidal composition may be obtained if a herbicide which functions as a photosystem II inhibitor is incorporated in a composition containing an agriculturally acceptable salt of N-phosphonomethylglycine and either diquat or paraquat. We have found that such compositions exhibit excellent visible early burndown symptoms in treated plants without excessive reduction in long term or re-growth control. In some instances and against some target species, the composition even combines excellent early burndown with quite unexpectedly increased long term control and reduction in re-growth.

Thus according to the present invention there is provided a herbicidal composition comprising (i) N-phosphonomethylglycine or an agriculturally acceptable salt thereof in combination with (ii) paraquat or diquat or a mixture thereof and (iii) a herbicide which functions as a photosystem II inhibitor.

The agriculturally acceptable salt of N-phosphonomethylglycine is preferably the sodium, ammonium, isopropylamine or trimethylsulphonium salt of N-phosphonomethylglycine (glyphosate trimesium).

The term "paraquat" as used herein includes any salt of 1,1'-dimethyl-4,4'-bipyridinium, including the dichloride and the bis(methyl sulphate). "Diquat" is commercially available in the form of the salt diquat dibromide.

As examples of herbicides which function as photosystem II inhibitors there may be mentioned diuron [3-(3,4-dichlorophenyl)-1,1-dimethylurea)], chlortoluron, isoproturon, linuron, tebuthiuron, bentazone, oxadiazon, bromacil, ametryne, atrazine, cyanazine, hexazinone, metribuzin, simazine, and terbuthylazine, all of which are commercially available herbicides. Especially preferred photosystem II inhibitors are diuron and cyanazine.

The proportion of paraquat, diquat or the mixture thereof in the composition of the present invention is preferably from 1 part by weight to 25 and especially from 3 to 20 parts by weight of paraquat, diquat or the mixture thereof per 100 parts by weight of the agriculturally acceptable salt of N-phosphonomethylglycine. A lower proportion of paraquat, diquat or the mixture thereof may be used but will tend to reduce the visible early burndown. Conversely a higher proportion of paraquat, diquat or the mixture thereof may be used but will tend to reduce the long term and re-growth control. A preferred proportion of paraquat, diquat or the mixture thereof in the composition of the present invention is from 5 parts by weight to 20 parts, for example from 5 to 10 parts by weight of paraquat, diquat or the mixture thereof per 100 parts by weight of the agriculturally acceptable salt of N-phosphonomethylglycine.

The proportion of the photosystem II inhibitor in the composition of the present invention is preferably from 10 to 10,000 parts by weight of photosystem II inhibitor per 100 parts by weight of paraquat, diquat or the mixture thereof, for example from 100 to 2000 parts by weight of photosystem II inhibitor per 100 parts by weight of paraquat, diquat or the mixture thereof. A lower proportion of the photosystem II inhibitor may be used but will tend to reduce the long term and re-growth control.

Expressed in terms of the agriculturally acceptable salt of N-phosphonomethylglycine, the ratio of agriculturally acceptable salt of N-phosphonomethylglycine to the photosystem II inhibitor is preferably from 50 to 200 parts by weight of photosytem II inhibitor per 100 parts of agriculturally acceptable salt of N-phosphonomethylglycine.

As examples of typical proportions of preferred compositions of the present invention there may be mentioned glyphosate trimesium: diquat (or paraquat): photosystem II inhibitor ratios of 10:1:5, 20:1:5, 10:1:10, 5:1:5, 20:1:10 and 20:1:20.

Compositions of the present invention are active against a broad range of weed species including monocotyledonous and dicotyledonous species. It is a further advantage of the present invention that the composition may show enhanced activity as compared with the agriculturally acceptable salt of N-phosphonomethylglycine against certain broad-leaf species. The compositions of the present invention are suitably applied directly to unwanted plants (post-emergence application).

Thus according to a further aspect of the present invention there is provided a process of severely damaging or killing unwanted plants, and more particularly a process of providing both early burdown and long-term and re-growth control of unwanted plants which comprises applying to the plants or to the growth medium of the plants a herbicidally effective amount of a composition of the present invention.

The compositions of the present invention may be used on their own to kill or severely damage plants, but are preferably used in the form of a liquid or solid composition.

Compositions of the present invention include both dilute compositions, which are ready for immediate use, and concentrated compositions, which require to be diluted before use, usually with water. Preferably the compositions contain from 0.01% to 90% by weight of the agriculturally acceptable salt of N-phosphonomethylglycine. Dilute compositions ready for use preferably contain from 0.01 to 2% of agriculturally acceptable salt of N-phosphonomethylglycine, while concentrated compositions may contain from 20 to 90% of agriculturally acceptable salt of N-phosphonomethylglycine, although from 20 to 70% is usually preferred.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution, suspension or dispersion of the active ingredients in water optionally containing a surface-active agent, or may comprise a solution or dispersion of the active ingredient in a water-immiscible organic solvent which is dispersed as droplets in water. Preferred active ingredients of the composition of the present invention are water-soluble herbicides or are readily suspended in water and it is preferred to use aqueous compositions and concentrates. In particular, glyphosate trimesium, paraquat and diquat are all readily soluble in water and diuron is readily suspended in water and the herbicidal composition is suitable either for tank mixing to produce a dilute composition ready for immediate use or for the formation of an aqueous concentrate.

Surface-active agents may be of the cationic, anionic, or non-ionic type or mixtures thereof. The cationic agents are, for example, quaternary ammonium compounds (e.g. cetyltrimethylammonium bromide). Suitable anionic agents are soaps; salts of aliphatic mono ester of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonyl- phenol (e.g. Agral 90) or octyl-cresol. Other non-ionic agents are the partial esters derived from long chain fatty acids and hexitol anhydrides, for example sorbitan monolaurate; the condensation products of the partial ester with ethylene oxide; the lecithins; and silicone surface active agents (water soluble surface active agents having a skeleton which comprises a siloxane chain e.g. Silwet L77). A suitable mixture in mineral oil is Atplus 411F.

Surfactants which are especially effective for use with aqueous compositions of agriculturally acceptable salts of N-phosphonomethylglycine are known to those skilled in the art. Examples include alkyl polyglucosides and ethoxylated amines such as ethoxylated tallow amines.

The aqueous solutions or dispersions may be prepared by dissolving the active ingredients in water or an organic solvent optionally containing wetting or dispersing agent(s) and then, when organic solvents are used, adding the mixture so obtained to water optionally containing wetting or dispersing agent(s). Suitable organic solvents include, for example, ethylene di-chloride, isopropyl alcohol, propylene glycol, diacetone alcohol, toluene, kerosene, methylnaphthalene, the xylenes and trichloroethylene, although as indicated above it is preferred to use an entirely aqueous system for compositions of the present invention.

The compositions for use in the form of aqueous solutions or dispersions are generally supplied in the form of a concentrate containing a high proportion of the active ingredients, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the agriculturally acceptable salt of N-phosphonomethylglycine. Dilute preparations ready for use may contain varying amounts of the agriculturally acceptable salt of N-phosphonomethylglycine depending upon the intended purpose; amounts of 0.01% to 10.0% and preferably 0.1% to 2%, by weight of agriculturally acceptable salt of N-phosphonomethylglycine are normally used.

Other additives and adjuvants may also be present in compositions of the present invention. Examples include anti-freeze agents such as ethylene glycol and propylene glycol; dyes; dispersants; rheological agents; anti-foam agents such as silicone based agents; and humectants such as ethylene glycol. Ammonium salts such as the sulphate may in certain circumstances enhance the activity of agriculturally acceptable salts of N-phosphonomethylglycine and may if desired be included in compositions of the present invention.

The rate of application of the composition of the invention will depend on a number of factors including, for example, the active ingredients chosen for use, the identity of the plants whose growth is to be inhibited and the formulations selected for use and whether the compound is to be applied for foliage or root uptake. As a general guide, however, an application rate of from 0.001 to 20 kilograms per hectare is suitable while from 0.025 to 10 kilograms per hectare may be preferred.

The compositions of the invention may also comprise one or more additional compounds which possess biological activity.

The compositions of the present invention may be supplied in pre-mixed form or may be tank mixed shortly before application.

The invention is illustrated by the following Example in which all parts and percentages are by weight unless otherwise indicated. Treatment rates (indicated for example as g/ha) are expressed in terms of the weight of active ingredient.

EXAMPLES 1 to 3

Compositions of the present invention were compared with compositions containing only glyphosate trimesium as active ingredient and with compositions containing only glyphosate trimesium and diquat as active ingredients.

Compositions were prepared from the following formulations:

A) An aqueous formulation containing 160 g/l glyphosate trimesium; 160 g/l alkylpolyglycoside surfactant; and 300 g/l ammonium sulphate.

B) An aqueous formulation containing 160 g/l glyphosate trimesium; 160 g/l alkylpolyglycoside surfactant; 300 g/l ammonium sulphate; and 8 g/l diquat.

C) A wettable powder formulation containing 800 g/kg of diuron and available commercially under the trade name KARMEX (KARMEX is a trademark of Du Pont).

The herbicidal activity of the compounds was tested as follows:

Required aliquots of each formulation were added to a 25 ml volumetric flask and made up to volume with deionised water. This was sprayed in three replicates onto young pot plants giving a volume rate equivalent to 200 l/ha. Plants of each test species were then returned to warm or temperate glasshouse environments as appropriate for optimal growth.

Damage to plants was assessed at intervals after spraying by comparison with untreated plants, on a 0–100% scale where 0% is no damage and 100% is complete kill. Statistical analysis was carried out using simple linear regression (least squares method) to produce values of the rate required for 50% damage (referred to as $ED_{50}$) or 90% damage (referred to as $ED_{90}$). Relative potencies of each treatment were then calculated.

The test species used and the relevant abbreviations are given in Table I.

In Comparison 1, the glyphosate trimesium formulation (A) was applied to the test species and was diluted to provide a series of rates spanning the range 62.5 to 2000 g/ha (for example 62.5; 125; 250; 500; 1000; 2000 g/ha). The damage to the plants was assessed visually at 2 days after treatment and then subsequently at 27 days after treatment.

In Comparison 2, glyphosate trimesium/diquat formulation (B) was applied to the test species and was diluted to provide a series of rates spanning the range 62.5 to 2000 g(glyphosate trimesium)/ha using the method of Comparison 1.

In Example 1, Diuron (formulation C) was added to formulation (B) (containing glyphosate trimesium and diquat in the constant proportion of 20 parts by weight of glyphosate of trimesium to 1 part by weight of diquat) such that, after dilution to provide a series of different rates spanning the range 62.5 to 2000 g(glyphosate trimesium)/ha, the diuron content of each such diluted compostion as applied to the plants corresponded to a constant rate of 250 g(diuron)/ha. The plants were assessed as in Comparison 1.

In Example 2, the procedure of Example 1 was followed except that the diuron content of each diluted composition as applied to the plants corresponded to a constant rate of 500 g(diuron)/ha.

In Example 3, the procedure of Example 1 was followed except that the diuron content of each diluted composition as applied to the plants corresponded to a constant rate of 1000 g(diuron)/ha.

In each test, the data for each series of rates of application was analysed statistically to determine the $ED_{50}$ for the data recorded at 2 days after treatment and the $ED_{90}$ for data recorded at 27 days after treatment respectively. The results are presented in Table II (A) and (B).

For comparison purposes, the relative potencies (ratio of $ED_{50}$ and $ED_{90}$ values respectively) are given in Table III (2 days after treatment) and Table IV (27 days after treatment) relative to Comparison 2 (the composition containing 20 parts by weight of glyphosate trimesium to 1 part by weight of diquat).

The following conclusions can be drawn from Table III:

1. Glyphosate trimesium on its own exhibits little visible activity against any species at 2 days after treatment.
2. The results at 2 days after treatment indicate that compositions of the present invention show no significant reduction in early burndown activity (as compared with the composition containing only glyphosate trimesium and diquat) in respect of SORHA, CYPRO, CHEAL, MATIN and POLAV. Whilst there is some reduction in early burndown activity (as compared with the composition containing only glyphosate trimesium and diquat) in respect of ELEIN, CONAR and EPHHL at all levels of diuron tested, significant early burndown is observed with all species in comparison with glyphosate trimesium alone.
3. At 27 days after treatment, the presence of diquat in compositions containing only glyphosate trimesium and diquat resulted in a reduction of potency relative to glyphosate trimesium for all species except AGRRE and MATIN. The addition of diuron reversed the adverse effects on all species. Furthermore, the compositions of the present invention actually showed a statistically significant increase in potency relative to glyphosate trimesium alone on CHEAL and POLAV at all levels of diuron; on CONAR and MATIN at levels of diuron in excess of 500 g/ha; and on AGRRE, LOLPE and EPHHL at levels of diuron in excess of 1000 g/ha.

TABLE I

| Abbreviations used for Test Plants | |
| --- | --- |
| AGRRE | Elymus repens |
| ELEIN | Eleusine indica |
| LOLPE | Lolium perenne |
| SORHA | Sorgum halepense |
| CYPRO | Cyperus rotundus |
| CHEAL | Chenopodium album |
| CONAR | Convolvulus arvensis |
| EPHHL | Euphorbia heterophylla |
| MATIN | Matricara perforata |
| POLAV | Polygonum aviculare |

TABLE II(A)

| | $ED_{50}$ values (g/ha) 2 Days after Treatment | | | | |
| --- | --- | --- | --- | --- | --- |
| SPECIES | Comparison 1 | Comparison 2 | Example 1 | Example 2 | Example 3 |
| AGRRE | >1000 | >1000 | >1000 | >1000 | >1000 |
| ELEIN | >1000 | 727 | 1176 | 1205 | 1515 |
| LOLPE | >1000 | >1000 | >1000 | >1000 | >1000 |
| SORHA | >1000 | 665 | 896 | 800 | 854 |
| CYPRO | >2000 | 2746 | 2948 | 2636 | 2905 |
| CHEAL | >1000 | 862 | 597 | 806 | 838 |
| CONAR | >2000 | 1277 | 2521 | 2429 | 2316 |
| EPHHL | >1000 | 822 | 1263 | 1100 | 1218 |

TABLE II(A)-continued

ED$_{50}$ values (g/ha) 2 Days after Treatment

| SPECIES | Comparison 1 | Comparison 2 | Example 1 | Example 2 | Example 3 |
|---|---|---|---|---|---|
| MATIN | >1000 | 618 | 795 | 646 | 661 |
| POLAV | >1000 | 805 | >1000 | >1000 | 1151 |

TABLE II(B)

ED$_{90}$ values (g/ha) 27 Days after Treatment

| SPECIES | Comparison 1 | Comparison 2 | Example 1 | Example 2 | Example 3 |
|---|---|---|---|---|---|
| AGRRE | 587 | 583 | 419 | 361 | >62.5 |
| ELEIN | 1535 | >1000 | >1000 | >1000 | 1535 |
| LOLPE | 907 | 983 | 513 | 472 | >62.5 |
| SORHA | 687 | 1357 | 1755 | 1800 | 735 |
| CYPRO | 3390 | >2000 | >2000 | >2000 | >2000 |
| CHEAL | 875 | 1487 | <125 | <125 | <62.5 |
| CONAR | 2701 | 3285 | 1137 | 244 | <125 |
| EPHHL | 296 | 425 | 177 | 118 | 93 |
| MATIN | 379 | 346 | 276 | <125 | <62.5 |
| POLAV | 741 | 1198 | <125 | <62.5 | <62.5 |

TABLE III

RELATIVE POTENCY AT 2 DAYS AFTER TREATMENT

| SPECIES | Comparison 1 | Comparison 2 | Example 1 | Example 2 | Example 3 |
|---|---|---|---|---|---|
| AGRRE | 0 | 1 | NRE | NRE | NRE |
| ELEIN | 0 | 1 | 0.62– | 0.60– | 0.48– |
| LOLPE | 0 | 1 | NRE | NRE | NRE |
| SORHA | 0 | 1 | 0.74 | 0.83 | 0.78 |
| CYPRO | 0 | 1 | 0.93 | 1.04 | 0.95 |
| CHEAL | 0 | 1 | 1.44 | 1.07 | 1.03 |
| CONAR | 0 | 1 | 0.51– | 0.53– | 0.55– |
| EPHHL | 0 | 1 | 0.65– | 0.75– | 0.68– |
| MATIN | 0 | 1 | 0.78 | 0.96 | 0.94 |
| POLAV | 0 | 1 | <1 | <1 | 0.70 |

0 = little activity from glyphosate trimesium
– = less potent than Comparison 2 (statistically significant)
NRE = Not Reliably Estimable

TABLE IV

RELATIVE POTENCY AT 27 DAYS AFTER TREATMENT

| SPECIES | Comparison 1 | Comparison 2 | Example 1 | Example 2 | Example 3 |
|---|---|---|---|---|---|
| AGRRE | 0.99 | 1 | 1.39 | 1.62* | >4** |
| ELEIN | 3.78 | 1 | 0.33 | 1.58 | 3.78* |
| LOLPE | 1.09 | 1 | 1.92 | 2.08* | >10** |
| SORHA | 1.98* | 1 | 0.77 | 0.75 | 1.85* |
| CYPRO | 1.78 | 1 | 0.60 | 0.62 | 1.14 |
| CHEAL | 1.70* | 1 | >8** | >8** | >16** |
| CONAR | 1.22 | 1 | 2.89* | 13.45** | >16** |
| EPHHL | 1.44 | 1 | 2.41* | 3.62* | 4.56* |
| MATIN | 0.99 | 1 | 1.26 | >4** | >8** |
| POLAV | >1.62* | 1 | >8** | >16** | >16** |

* = more potent than Comparison 2 (statistically signficant)
** = more potent than Comparison 1 and Comparison 2 (statistically significant)

EXAMPLE 4

The general procedure of Examples 1 to 3 was repeated using formulations prepared from the following compositions:

A) An aqueous formulation containing 480 g/l glyphosate trimesium and 240 g/l alkylpolyglycoside surfactant.

B) An aqueous formulation containing 200 g/l diquat as diquat dibromide.

C) An aqueous formulation containing 200 g/l paraquat as paraquat dichloride.

D) A wettable powder formulation containing 800 g/kg of diuron and available commercially under the trade name KARMEX (KARMEX is a trademark of Du Pont).

A mixture (formulation (v) in Table V) according to the invention was prepared by mixing (A) and (B) and (D) and was sprayed at a rate corresponding to 500 g/ha glyphosate trimesium, 100 g/ha diquat and 500 g/ha diuron.

The individual components were sprayed at corresponding individual rates as follows:

500 g/ha glyphosate trimesium—formulation (i) in Table V 100 g/ha diquat—formulation (ii) in Table V and 500 g/ha diuron—formulation (iv) in Table V.

A mixture (formulation (vi) in Table V) according to the invention was prepared by mixing (A) and (C) and (D) and was sprayed at a rate corresponding to 500 g/ha glyphosate trimesium, 100 g/ha paraquat and 500 g/ha diuron.

The individual components were sprayed at corresponding individual rates as follows:

500 g/ha glyphosate trimesium—formulation (i) in Table V 100 g/ha paraquat—formulation (iii) in Table V and 500 g/ha diuron—formulation (iv) in Table V.

The results at 22 days after treatment are presented in TABLE V and are given in terms of % herbicidal effect relative to the control (mean of three replicates) where 0% represents no herbicidal effect and 100% indicates indicates complete kill.

TABLE V

HERBICIDAL EFFECT (%)
AT 22 DAYS AFTER TREATMENT

| SPECIES | FORMULATION | | | | | |
|---------|-----|------|-------|------|-----|------|
|         | (i) | (ii) | (iii) | (iv) | (v) | (vi) |
| AGRRE   | 85  | 0    | 37    | 67   | 93  | 100  |
| ELEIN   | 89  | 7    | 43    | 28   | 83  | 82   |
| SORHA   | 98  | 33   | 30    | 0    | 45  | 94   |
| CYPRO   | 3   | 10   | 22    | 0    | 13  | 92   |
| CHEAL   | 83  | 8    | 65    | 99   | 100 | 100  |
| CONAR   | 52  | 15   | 25    | 65   | 92  | 98   |
| EPHHL   | 74  | 5    | 8     | 2    | 77  | 88   |
| MATIN   | 87  | 100  | 100   | 35   | 100 | 100  |
| POLAV   | 89  | 15   | 7     | 94   | 100 | 100  |

EXAMPLE 5

The general procedure of Example 4 was repeated using formulations prepared from the compositions A, B, C and D.

A mixture (formulation (vii) in Tables VI and VII) according to the invention was prepared by mixing (A) and (C) and (D) and was sprayed at a rate corresponding to 500 g/ha glyphosate trimesium, 100 g/ha paraquat and 500 g/ha diuron.

The individual components were sprayed at corresponding individual rates as follows:

500 g/ha glyphosate trimesium—formulation (i) in Table V;

100 g/ha paraquat—formulation (ii) in Table V; and 500 g/ha diuron—formulation (iii) in Table V.

By way of further comparison, the following two-component mixtures were sprayed at corresponding rates as follows:

500 g/ha glyphosate trimesium and 100 g/ha paraquat—formulation (iv) in Table V;

500 g/ha glyphosate trimesium and 500 g/ha diuron—formulation (v) in Table V; and 100 g/ha paraquat and 500 g/ha diuron—formulation (vi) in Table V.

The results at 3 and 23 days after treatment respectively are presented in TABLES VI and VII and are given in terms of mean % herbicidal effect relative to the control.

TABLE VI

HERBICIDAL EFFECT (%)
AT 3 DAYS AFTER TREATMENT

| SPECIES | FORMULATION | | | | | | |
|---------|-----|------|-------|------|-----|------|-------|
|         | (i) | (ii) | (iii) | (iv) | (v) | (vi) | (vii) |
| ELEIN   | 23  | 67   | 0     | 77   | 29  | 64   | 81    |
| SORHA   | 37  | 65   | 0     | 81   | 27  | 58   | 81    |
| CONAR   | 0   | 55   | 0     | 55   | 0   | 25   | 25    |
| CHEAL   | 20  | 18   | 0     | 60   | 18  | 69   | 79    |

TABLE VII

HERBICIDAL EFFECT (%)
AT 23 DAYS AFTER TREATMENT

| SPECIES | FORMULATION | | | | | | |
|---------|-----|------|-------|------|-----|------|-------|
|         | (i) | (ii) | (iii) | (iv) | (v) | (vi) | (vii) |
| ELEIN   | 85  | 42   | 28    | 62   | 67  | 79   | 93    |
| SORHA   | 97  | 50   | 0     | 47   | 77  | 57   | 53    |
| CONAR   | 49  | 32   | 63    | 37   | 84  | 76   | 98    |
| CHEAL   | 62  | 8    | 76    | 48   | 98  | 99   | 99    |

It can be seen that excellent early burndown is obtained when using the formulation of the present invention (vii) whilst long-term control is enhanced in respect of most species. In contrast, the comparison formulations (i) to (vi) either provide insufficient early burndown or provide effective early burndown only at the cost of long-term control.

EXAMPLE 6

A number of photosystem II inhibitors were investigated using the general method of Eample 4. The results obtained at 3 days after treatment and 23 days after treatment are shown in Tables VIII and IX respectively where the formulations used are as follows and the rates of application expressed in g/ha are based on the weight of active ingredient.

Formulations based on the single active components were compared as follows:

(i) Glyphosate trimesium (composition A in Example 4) applied at 500 g/ha.
(ii) Paraquat (composition C in Example 4) applied at 100 g/ha
(iii) Ametryne (GESPAX 800 g/kg wettable powder - GESPAX is a trademark of Ciba-Geigy AG) applied at 500 g/ha
(iv) Bentazone (BASAGRAN 480g/l liquid - BASAGRAN is a trademark of BASF AG) applied at 500 g/ha
(v) Cyanazine (BLADEX 500 g/kg wettable powder - BALDEX is a trademark of Shell) applied at 500 g/ha
(vi) Diuron (Composition D in Example 4) applied at 500 g/ha A formulation (vii) based on a mixture of glyphosate trimesium and paraquat was applied at 500 g/ha and 100 g/ha respectively by way of further comparison.

Compositions according to the invention were prepared by mixing glyphosate trimesium, paraquat and the photosystem II inhibitor and were sprayed at rates corresponding to the following:

(viii) glyphosate trimesium (500 g/ha), paraquat (100 g/ha) and ametryne (500 g/ha)
(ix) glyphosate trimesium (500 g/ha), paraquat (100 g/ha) and bentazone (500 g/ha)
(x) glyphosate trimesium (500 g/ha), paraquat (100 g/ha) and cyanazine (500 g/ha)
(xi) glyphosate trimesium (500 g/ha), paraquat (100 g/ha) and diuron (500 g/ha)

TABLE VIII

HERBICIDAL EFFECT (%) AT 3 DAYS AFTER TREATMENT

| SPECIES | (i) | (ii) | (iii) | (iv) | (v) | (vi) | (vii) | (viii) | (ix) | (x) | (xi) |
|---|---|---|---|---|---|---|---|---|---|---|---|
| ELEIN | 32 | 72 | 15 | 10 | 12 | 0 | 77 | 80 | 70 | 83 | 72 |
| SORHA | 35 | 83 | 10 | 0 | 5 | 0 | 87 | 88 | 77 | 81 | 86 |
| CHEAL | 17 | 40 | 18 | 17 | 13 | 5 | 76 | 81 | 69 | 78 | 79 |
| CONAR | 7 | 43 | 2 | 3 | 3 | 3 | 63 | 25 | 10 | 33 | 28 |

TABLE IX

HERBICIDAL EFFECT (%) AT 23 DAYS AFTER TREATMENT

| SPECIES | (i) | (ii) | (iii) | (iv) | (v) | (vi) | (vii) | (viii) | (ix) | (x) | (xi) |
|---|---|---|---|---|---|---|---|---|---|---|---|
| ELEIN | 80 | 43 | 25 | 12 | 88 | 35 | 45 | 55 | 45 | 100 | 48 |
| SORHA | 95 | 65 | 28 | 13 | 58 | 0 | 52 | 45 | 27 | 97 | 59 |
| CHEAL | 57 | 17 | 100 | 55 | 100 | 100 | 81 | 91 | 91 | 100 | 100 |
| CONAR | 45 | 13 | 12 | 32 | 87 | 93 | 35 | 45 | 66 | 97 | 91 |

EXAMPLE 7

This Example illustrates the use of the sodium salt of N-phosphonomethylglycine in the composition of the present invention The sodium salt of N-phosphonomethylglycine was used in the form of the commercially available formulation ROUNDUP Dry (ROUNDUP is a trademark of Monsanto Company).

The following formulations were applied at the indicated rates:

(i) The sodium salt of N-phosphonomethylglycine, applied at a rate of 500 g/ha based on active ingredient (as the sodium salt)
(ii) A mixture of the sodium salt of N-phosphonemethylglycine and paraquat applied at a rate of 500 g/ha and 50 g/ha respectively.
(iii) A mixture according to the invention of the sodium salt of N-phosphonemethylglycine, paraquat and cyanazine applied at a rate of 500 g/ha, 50 g/ha and 250 g/ha respectively.

The formulations were evaluated using the general method of Example 4 against the following species:

DIGSA *Digitaria sanguinalis*
ECHCG *Echinochloa crus-galli*
LOLMU *Lolium multiflorum*
SETVI *Setaria viridis*
TRZAW Wheat (*Triticum aestivum*)
CYNDA *Cynodon dactylon*
AMARE *Amaranthus retroflexus*
GALAP *Galium aparine*
MATIN *Matricaria perforata*
POROL *Portulaca oleracea*
SINAR *Sinapis arvensis*
STEME *Stellaria media*
VERPE *Veronica persicaria*
VIOAR *Viola arvensis*

The results obtained, expressed in terms of the % herbicidal kill at 3 days after treatment and 23 days after treatment are given in Tables X and XI respectively.

TABLE X

HERBICIDAL EFFECT (%) AT 3 DAYS AFTER TREATMENT

| | FORMULATION | | |
|---|---|---|---|
| SPECIES | (i) | (ii) | (iii) |
| DIGSA | 47 | 81 | 90 |
| ECHCG | 43 | 79 | 85 |
| LOLMU | 18 | 67 | 67 |

TABLE X-continued

HERBICIDAL EFFECT (%)
AT 3 DAYS AFTER TREATMENT

| SPECIES | FORMULATION | | |
|---|---|---|---|
| | (i) | (ii) | (iii) |
| SETVI | 57 | 93 | 91 |
| TRZAW | 7 | 38 | 15 |
| CYNDA | 0 | 5 | 8 |
| AMARE | 42 | 98 | 73 |
| GALAP | 15 | 17 | 38 |
| MATIN | 23 | 83 | 58 |
| POROL | 8 | 88 | 82 |
| SINAR | 8 | 47 | 25 |
| STEME | 13 | 88 | 63 |
| VERPE | 8 | 97 | 75 |
| VIOAR | 7 | 71 | 17 |

TABLE XI

HERBICIDAL EFFECT (%)
AT 23 DAYS AFTER TREATMENT

| SPECIES | FORMULATION | | |
|---|---|---|---|
| | (i) | (ii) | (iii) |
| DIGSA | 95 | 80 | 85 |
| ECHCG | 70 | 49 | 89 |
| LOLMU | 93 | 87 | 100 |
| SETVI | 99 | 100 | 100 |
| TRZAW | 52 | 61 | 90 |
| CYNDA | 40 | 15 | 15 |
| AMARE | 96 | 100 | 100 |
| GALAP | 80 | 84 | 100 |
| MATIN | 100 | 94 | 100 |
| POROL | 45 | 99 | 100 |
| SINAR | 74 | 67 | 99 |
| STEME | 100 | 100 | 100 |
| VERPE | 100 | 100 | 100 |
| VIOAR | 86 | 96 | 100 |

I claim:

1. A herbicidal composition comprising (i) N-phosphonomethylglycine or an agriculturally acceptable salt thereof in combination with (ii) paraquat or diquat or a mixture thereof and (iii) a herbicide which functions as a photosystem II inhibitor.

2. A composition according to claim 1 wherein the agriculturally acceptable salt of N-phosphonomethylglycine is selected from the group consisting of the sodium, ammonium, isopropylamine and trimethylsulphonium salt.

3. A composition according to claim 1 wherein the herbicide which functions as a photosystem II inhibitor is selected from the group consisting of diuron, chlortoluron, isoproturon, linuron, tebuthiuron, bentazone, oxadiazon, bromacil, ametryne, atrazine, cyanazine, hexazinone, metribuzin, simazine and terbuthylazine.

4. A composition according to claim 1 wherein the proportion of paraquat, diquat or the mixture thereof in the composition is from 1 part by weight to 25 of paraquat, diquat or the mixture thereof per 100 parts by weight of the agriculturally acceptable salt of N-phosphonomethylglycine.

5. A composition according to claim 4 wherein the proportion of paraquat, diquat or the mixture thereof in the composition is from 3 parts by weight to 20 parts by weight of paraquat, diquat or the mixture thereof per 100 parts by weight of the agriculturally acceptable salt of N-phosphonomethylglycine.

6. A composition according to claim 4 wherein the proportion of paraquat, diquat or the mixture thereof in the composition is from 5 parts by weight to 20 parts by weight of paraquat, diquat or the mixture thereof per 100 parts by weight of the agriculturally acceptable salt of N-phosphonomethylglycine.

7. A composition according to claim 1 wherein the proportion of the photosystem II inhibitor in the composition is from 10 to 10,000 parts by weight of photosystem II inhibitor per 100 parts by weight of paraquat, diquat or the mixture thereof.

8. A composition according to claim 7 wherein the proportion of the photosystem II inhibitor in the composition is from 100 to 2000 parts by weight of photosystem II inhibitor per 100 parts by weight of paraquat, diquat or the mixture thereof.

9. A composition according to claim 1 wherein the proportion of the photosystem II inhibitor to the agriculturally acceptable salt of N-phosphonomethylglycine is from 50 to 200 parts by weight of photoystem II inhibitor per 100 parts of agriculturally acceptable salt of N-phosphonomethylglycine.

10. A composition according to claim 1 which additionally includes ammonium sulphate.

11. A process of severely damaging or killing unwanted plants which comprises applying to the plants or to the growth medium of the plants a herbicidally effective amount of a composition according to claim 1.

* * * * *